United States Patent [19]

Roy et al.

[11] Patent Number: 5,686,270

[45] Date of Patent: Nov. 11, 1997

[54] PRODUCTION OF ANTIGENS BY SELF-ASSEMBLY OF POLYPEPTIDE COMPONENTS

[75] Inventors: Polly Roy; Timothy J. French, both of Oxford, England

[73] Assignees: Oravax, Inc., Cambridge, Mass.; Natural Environmental Research Council, Swindon, England

[21] Appl. No.: 493,112

[22] Filed: Jun. 21, 1995

Related U.S. Application Data

[63] Continuation of Ser. No. 201,707, Feb. 25, 1994, abandoned, which is a continuation of Ser. No. 853,695, filed as PCT/GB90/01049, Jul. 6, 1990, abandoned.

[30] Foreign Application Priority Data

Jul. 7, 1989 [GB] United Kingdom ............... 8915571

[51] Int. Cl.[6] .................. C12N 5/06; C12N 15/06; C12N 15/63; C12P 21/02
[52] U.S. Cl. ............... 435/71.1; 435/172.3; 435/320.1; 435/948; 935/23; 935/24; 935/34; 935/57; 935/70
[58] Field of Search .................. 435/69.1, 69.3, 435/69.7, 70.1, 70.3, 240.2, 240.21, 172.3, 71.1, 320.1; 514/2; 530/260, 350

[56] References Cited

FOREIGN PATENT DOCUMENTS

| | | |
|---|---|---|
| 0279661 | 8/1988 | European Pat. Off. . |
| 0305087 | 3/1989 | European Pat. Off. . |

OTHER PUBLICATIONS

O'Reilly et al. 1988 Journal of Virology 62(9):3109–3119.

*Primary Examiner*—Brian R. Stanton
*Attorney, Agent, or Firm*—Nixon & Vanderhye

[57] ABSTRACT

Antigens are produced by self-assembly of polypeptide components. The production of bluetongue virus antigens (BTV) in the form of assembled particles comprising separate polypeptide components, particularly proteins VP2, VP3, VP5 and VP7 is described.

4 Claims, 10 Drawing Sheets

Fig. 1A

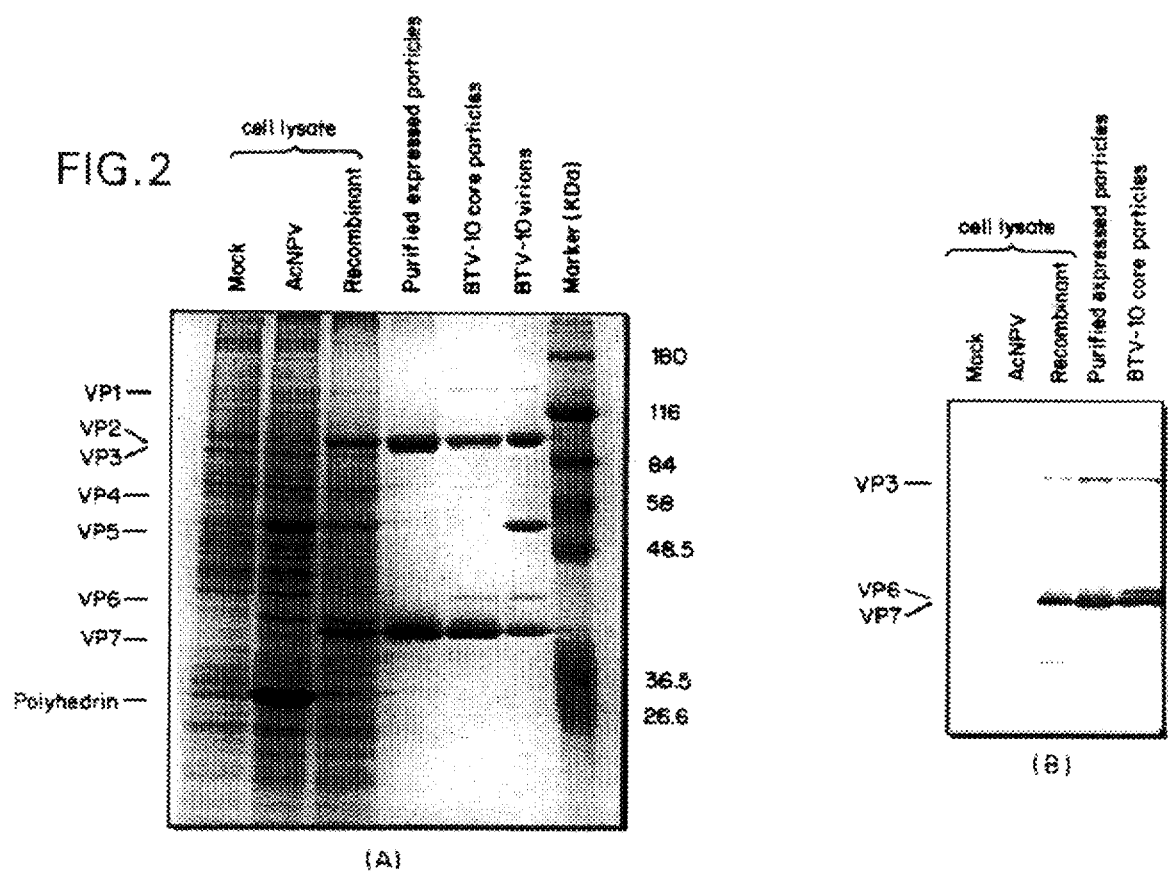

PRODUCTION OF ANTIGENS BY SELF-ASSEMBLY OF POLYPEPTIDE COMPONENTS

This is a Rule 62 continuation of application Ser. No. 08/210,707, filed 25 Feb. 1994, now abandoned, which is a Rule 62 continuation of application Ser. No. 07/853,695, filed as PCT/GB90/01049, Jul. 6, 1990, now abandoned.

This invention relates to the production of antigens by self-assembly of polypeptide components and particularly, but not exclusively to the production of bluetongue virus antigens (BTV) in the form of assembled particles comprising separate polypeptide components.

BACKGROUND OF THE INVENTION

Many virus particles, including bluetongue virus (BTV) consist of a nucleic acid (DNA or RNA) packaged together with a plurality of polypeptide components. The latter contribute to the antigenic properties of the virus and constitute the key components of vaccines and diagnostic test kits. Virus assembly involves highly specific interactions between the component protein species within the matrix of the host cell. As such viral morphogenesis provides a model for the study of cellular processes of macromolecular interaction.

To date, only single-shelled virus-like particles or cores have been assembled following the expression of one or two viral genes. Thus empty, single-shelled virus particles have been assembled for a number of different viruses from their appropriate structural proteins both in vivo (e.g. Hepatitis B) and in vitro (e.g. Rotavirus). In each of these examples the particles were organised from a single species of polypeptide. Recently empty polio virus particles containing three different protein species have been synthesized in vivo, however, the coding information for these proteins was provided by translation of a single mRNA.

Viral structures which contain multiple polypeptide species encoded by separate genes (e.g. BTV) present a more difficult and challenging objective. Formation of such structures, and evaluation the interactions of their protein components can be attempted but this may introduce artifacts. Synthesis of the individual proteins in eukaryotic cells by an expression system which mimics the natural situation of macromolecular interactions would be desirable, but hitherto, this has proved unatainable in practice.

Gene cloning and expression have proved to be powerful tools for assessing the structural and/or functional roles of individual proteins. The natural progression for future studies will be the examination of multi-protein 'structures' such as viruses or enzyme complexes. The assembly of virus-like particles following the synthesis of their component proteins is an area which presents a number of opportunities. For example, the stages of viral assembly, the contributions of individual components to that process, and the sites and nature of viral protein interactions can be studied. An increased understanding of viral morphogenesis may aid the development of antiviral agents which specifically interfere with the assembly process. Intact virus-like particles could also prove useful as vaccines if epitopes are presented in authentic conformations.

DESCRIPTION OF THE INVENTION

It has now been found that recombinant baculoviruses may be used to overcome these problems. Thus it has been found that by expressing, in susceptible insects or insect cells, proteins having a capacity to self-assemble, the polypeptides are able to form assembled antigen particles, which in many instances resemble the native viruses themselves, both in morphology and antigenic properties.

Thus according to the invention there is provided a process for the production of antigen particles by self-assembly of separate polypeptides, which comprises transforming a host with at least one recombinant expression vector wherein at lest one of the vectors has a DNA insert coding for one or more of said polypeptides whereby each of the polypeptides is expressed, and self-assembly of said polypeptides occurs with formation of said antigen particles.

The process of the invention is not restricted to any particular expression system and the host cells may be prokaryotic or eukaryotic (including, e.g. yeast or animal cells). Preferably however, the host comprises of susceptible insect or insect cells and said expression vector in a baculovirus expression vector.

Preferably, susceptible insects or insect cells are infected with a baculovirus expression vector having a DNA insert coding for each of said polypeptides.

More specifically, the present invention relates to the simultaneous expression of major Bluetongue virus (BTV) structural proteins in insect cells using multiple recombinant baculoviruses. The expressed polypeptides assembled to form non-infectious, double-shelled, virus-like particles of the same size and appearance as authentic BTV virions. Antibodies raised to the expressed particles contained very high titres of neutralizing activity against the homologous BTV serotypes. These results indicate the potential of this technology for the study of complex multiprotein structures, as well as the development of a new generation of viral vaccines.

There are numerous reports of high level expression of foreign proteins by recombinant baculoviruses (reviewed Luckow & Summers), and insect cells have been demonstrated to provide an appropriate environment for the accurate expression of foreign polypeptides. However, until recently a major limitation of baculoviruses has been that simultaneous expression of several proteins within a single cell requires co-infection with two recombinant viruses, each containing a single foreign gene.

Success by this approach is dependent upon achieving an efficient infection at a multiplicity of 5 or more pfu/cell (plaque forming units) for each virus. This requires large amounts of high titre virus stocks and means that scaling up to large cultures, should it be required, is impractical. To overcome these problems multiple expression vectors which allow the construction of recombinant viruses expressing a number of foreign gene products simultaneously have been designed and constructed.

Typical vectors incorporate two copies of the polyhedrin promoter and transcription termination sequences, although other duplicated promoters may also be used.

One system utilising such a vector is the subject of International Patent Application WO89/01518 and is particularly useful in carrying out the method of the present invention.

Thus, in carrying out the process of the invention, the so-called "multiple expression system" which is the subject of International Patent Application WO89/01518 is advantageously used to express the aforementioned separate polypeptides. The procedures described in WO89/01518 utilize a plasmid designated pAcVC3 which has been deposited under the provisions of the Budapest Treaty on Aug. 7, 1987 at the National Collection of Industrial Bacteria located at 23 St. Machar Drive, Aberdeen, Scotland AB24 3RY, United Kingdom under Accession No. NCIB12516.

pAcVC3, contains duplicated copies of the polyhedrin transcriptional machinery from *Autographa californica* nuclear *Spodoptera frugiperda* insect cells. In pAcVC3, a unique enzyme restriction site located downstream of each promoter allows for the insertion of two foreign genes, each of which will be placed under the control of its own copy of the polyhedrin transcriptional machinary. The promoters are present in opposite orientations to minimize the possibility of homologous sequence recombination and excision of one or other of the foreign genes.

Thus in carrying out the method of the present invention, each of the DNA inserts which codes for one of said separate polypeptides preferably comprises part of a polypeptide expression sequence (PES) wherein each PES includes (i) a transcriptional promoter, (ii) a DNA sequence coding for one of said polypeptides and (iii) a transcriptional termination site. Preferably, respective PESs contain DNA sequences (ii) coding for different polypeptides are arranged in the opposite sense on separate strands of DNA.

The promoters used in the method of the invention are not critical, but preferably expression of each of said DNA inserts is under the control of a so-called "late" or "very late" promoter such as the AcNPV polyhedrin or p10 promoters.

Applying these techniques to viruses with structures derived from the translation products of more than one mRNA, co-expression of different genes has enabled essentially 'complete' empty particles to be assembled.

In carrying out the method of the invention, according to one embodiment, the L3 and M7 genes of bluetongue virus (BTV), which code for the two major structural core proteins VP3 and VP7 respectively, may be inserted into a baculovirus dual expression transfer vector and a recombinant baculovirus expressive both foreign genes isolated following in vivo recombination with wild-type AcNPV DNA.

BTV is an arthopod-borne virus causing disease in sheep and cattle. It is prevalent in many areas of the world, and is of economic importance to the livestock industry. The virus is a member of the Orbivirus genus in the family Reoviridae, with ten segments of double-stranded RNA located in a core particle consisting of two major proteins VP3 and VP7 together with three major proteins VP1, VP4 and VP6. An outer capsid of two major proteins VP2 and VP5 surrounds the core. The function(s) of the core proteins have not been determined, and little is known about their interactions and stoichiometric arrangements.

Appreciation of such factors is obviously important in order to understand the morphogenesis of a complex virus such as BTV. Recent cryoelectron microscopy studies suggests that the core of BTV consists of a nucleoprotein centre surrounded by two distinct protein layers, each of which is composed of a single polypeptide species. Immunogold analysis indicates that VP7 forms the outer-most layer, which is attached to a framework of VP3.

Utilising such a procedure, *Spodoptera frugiperda* cells infected with such a recombinant have been shown to synthesize spherical core-like particles which are the same in size, appearance and stoichiometric arrangement of VP3 to VP7 as authentic BTV cores. This result is significant not just in the context of increasing understanding of BTV morphogenesis, but also for gene expression per se.

The correct assembly of a complex structure in vivo by a recombinant baculovirus expressing multiple foreign genes indicates the potential of this technique to approach fundamental questions in cell biology involving multimolecular structures.

As indicated, the method of the invention is of particular use in producing antigenically active particles derived from bluetongue virus (BTV) proteins, but may be used in production of other antigen particles capable of self-assembly. These include bluetongue virus proteins other than VP3 and VP7.

In a particularly preferred embodiment which is further described and claimed in our copending International Patent Application No. PCT/GB/90/01047, filed Jul. 6, 1990 (claiming priority from GB 8915572.5), the antigenically active particles includes at least one of proteins VP2 and VP5.

VP2 and VP5 are termed "outer" proteins in the bluetongue virus and have the role of binding receptors on lost cells and mediating in the passage of virions into the host cell's interior.

VP2 is an important antigen as it is effective in raising neutralizing antibodies and can be used as a vaccine component. By constructing a VP2-containing antigen particle according to the invention superior vaccines can be produced that can be used without adjuvants.

Production of assembled antigen particles according to the invention can be used to produce antigen for use in the manufacture of vaccines and components of diagnostic test kits.

So-called "chimeric" antigens may be produced according to the invention wherein the individual polypeptides of the assembled particles may be of different serotypes of a common virus species or they may be antigens derived from different virus species. Examples include the different serotypes of bluetongue virus. Thus one of the polypeptides may be derived from one serotype and one from another.

The production of antigen in the form of self-assembled particles, further permits the purification of the antigen particles by techniques that-make use of characteristic features of the particles such as density and/or size. Thus the particles produced by the method of the invention may be more readily purified by sucrose-density centrifugation than the individual polypeptide components thereof.

BRIEF DESCRIPTION OF THE DRAWINGS

The invention will now be described in more detail with reference to the accompanying drawings, in which FIGS. 1A and 1B show a construction diagram of a dual express transfer vector showing the appropriate manipulations for the insertion of BTV L3 and M7 genes;

FIGS. 2A and 2B show SDS-PAGE results stained with Coomassie Blue (FIG. 2A) or electroblotted onto immobilon membrane and reacted with rabbit anti-BTV-10 serum (FIG. 2B);

FIG. 3B shows purified esterified expressed particles (3) as compared with authentic BTV core particles (FIG. 3C);

EXAMPLES

In the following examples Example 1 describes the synthesis of BTV core particles from these components, utilizing a dual recombinant baculovirus containing the L3 and M7 genes which encode the VP3 and VP7 polypeptides. Example 2 describes the production of BTV core-like particles by co-expression of VP2, VP3, VP5 and VP7.

Example 1

Figure 1A:
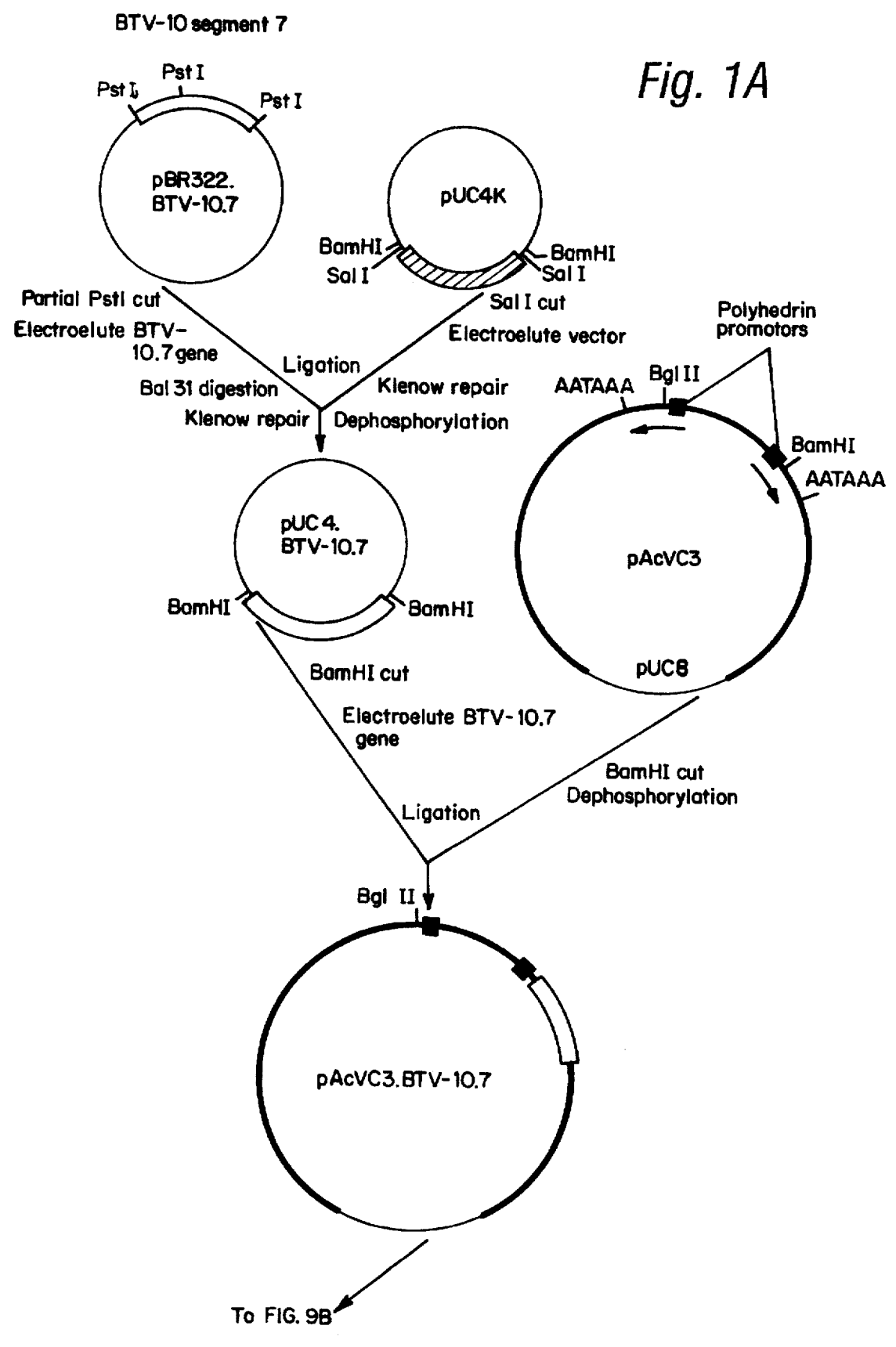
Figure 1B:
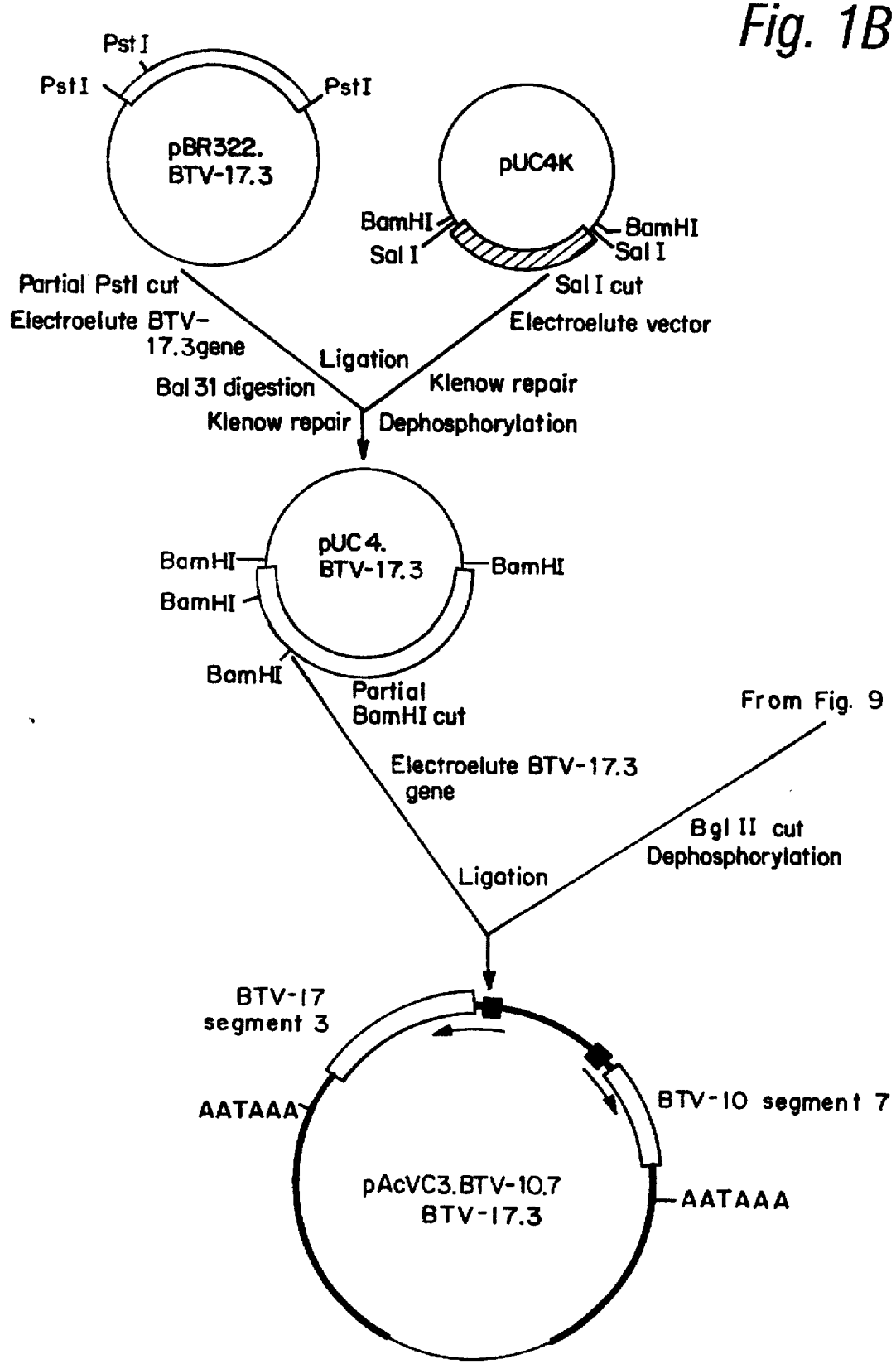

The construction of recombinant expression vector pAcVC3.BTV-10.7.BTV-17.3 is illustrated in FIG. 1.

The initial step for the expression of the BTV genes was to synthesize cDNA copies of the double stranded RNA L3 and M7 segments. Although these were isolated from different serotypes (17 and 10 respectively), the L3 gene is very highly conserved with an amino acid homology of greater than 99%.

Homopolymeric tails introduced to aid the cloning procedure were removed by limited Bal31 exonuclease digestion before insertion of the genes into the pAcVc3 transfer vector. Recombinant baculoviruses were prepared by the established procedure of co-transfecting S. frugiperda cells with the dual expression plasmid DNA and wild-type AcNPV DNA.

Progeny viruses were titrated using confluent monolayers of S. frugiperda cells and putative recombinants selected on the basis of their polyhedrin negative phenotype (ca 0.1% fequency). After successive rounds of plaque purification of high titre viral stock was prepared. S. frugiperda cells infected with the recombinant baculovirus synthesized two unique proteins species in place of the 29 kDa polyhedrin protein seen in wild-type AcNPV infected cells (FIG. 2A).

The sizes of the expression proteins agree with those expected for VP3 and VP7 calculated from their amino acid compositions (103,226 KDa and 385,48 KDa respectively). Confirmation that these expressed proteins represented authentic BTV proteins was provided by Western blot analysis with antisera raised to BTV-10 virus particles (FIG. 2B).

VP3 is a group specific antigen and is recognised by antisera to all BTV serotypes. Electron micrographs of S. frugiperda cells infected with the recombinant showed large aggregates of foreign material in the cytoplasm (FIG. 3) which, under high magnification, appeared to consist of spherical particles.

Figure 3A:
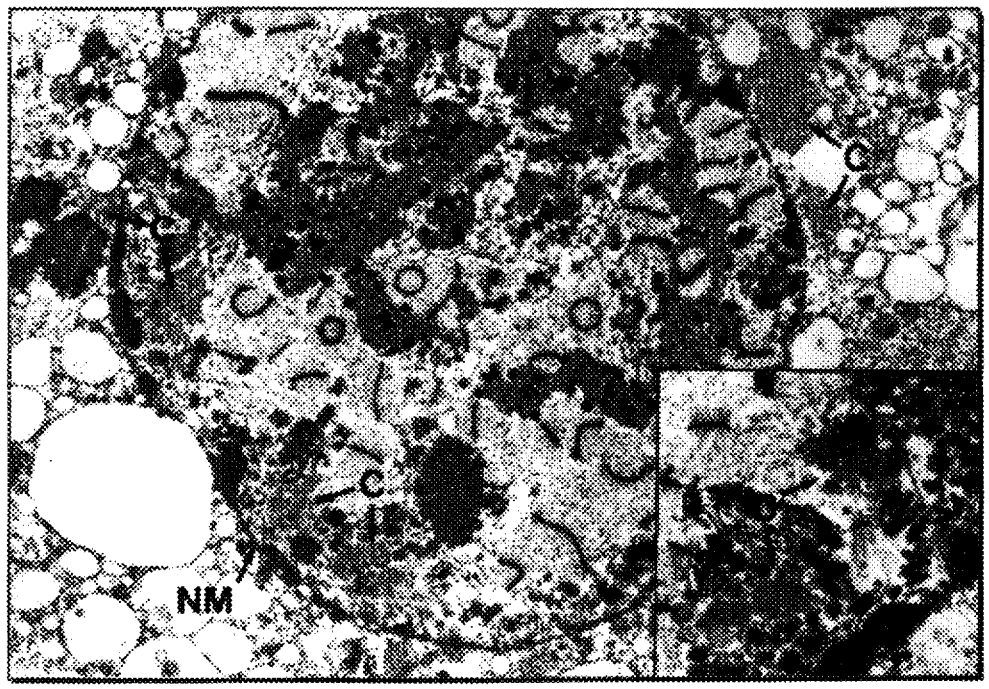
FIGS. 3A, 3B and 3C are electron micrographs of empty BTV core particles synthesized by a recombinant baculovirus containing *S. frugiperda* cells infected with the recombinant (1) or wild-type AcNPV virus (2)
Figure 3B:
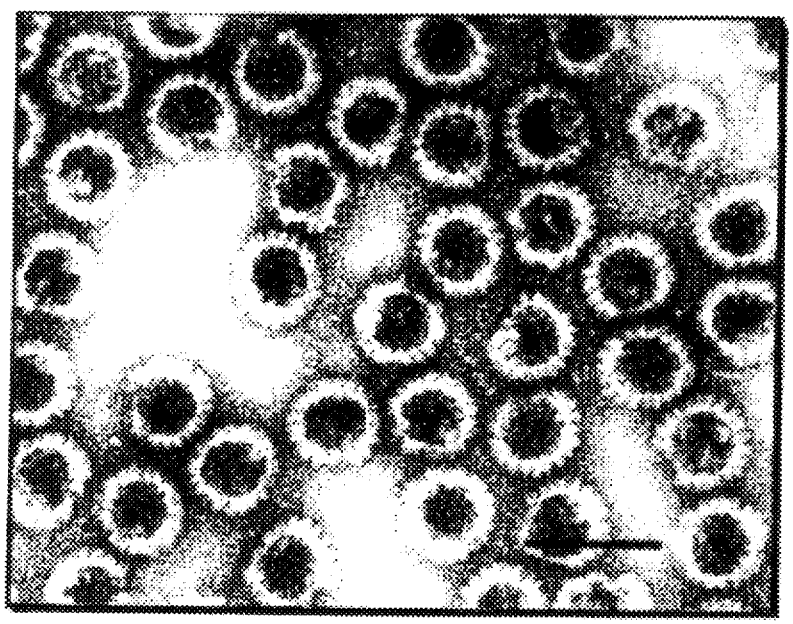
Figure 3C:
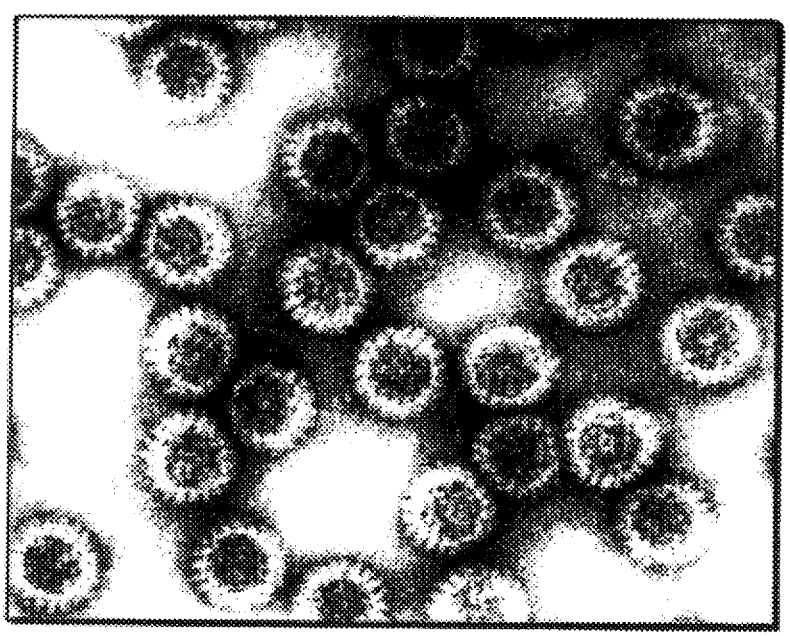

This expressed material was isolated by lysing the cells with NP40, and purification on a discontinuous sucrose gradient. When examined under the electron microscope the material was found to consist of empty core-like particles whose size and appearance were essentially identical to authentic BTV core particles prepared from BTV-infected BHK cells (FIG. 3).

How precisely the expressed particles resembled their viral counterparts was further appraised by calculation of the VP3 and VP7 stoichimetry. S. frugiperda cells infected with the recombinant baculovirus were pulse-labelled at 24 h p.i. with [$^{35}$S]methionine and, after purification on discontinuous sucrose gradients, the labelled particles were dissociated, and the components separated by SDS-PAGE. The bands of VP7 and VP3 were located by autoradiography, excised and counted in a liquid scintilation cocktail containing a tissue solubilizer. Since the number of methionine residues in each protein is known their stoichiometry could be calculated. After averaging the results from two different experiments, a value of 15 VP7 molecules to 2 VP3 molecules was obtained. This exactly matches the stoichiometry of these components in BTV core particles as determined by labelling with [$^{14}$C] amino acids. Recent evidence from our laboratory indicates that 780 copies of VP7 are present per core particle, which based upon a 15:2 molecular arrangement, denotes the cores contain 104 copies of VP3.

The synthesis of empty BTV core particles from the major core proteins VP3 and VP7 reveals some important aspects of BTV morphology. It can be concluded from the fact that core-like particles were synthesized that their formation is not dependent on the presence of the three minor core proteins, nor the BTV double-stranded RNA. In addition, the three BTV non-structural proteins (NS1, NS2, NS3) are not required to assist, or direct the assembly of the VP3 and VP7 proteins to form stoichiometrically correct empty particles.

The results obtained provide the opportunity for more detailed research of viral morphogenesis and the interactions of structural proteins, as well as testing antivirals that may inhibit morphogenic pathways.

Example 2

When used to immunize animals, the single-shelled core-like particles produced according to Example 1 do not protect against subsequent BTV infection as the epitopes that elicit neutralizing antibodies are present on the outer capsid protein VP2. Since a recombinant baculovirus expressing VP2 has been constructed co-infection experiments were initially undertaken with the VP3 ane VP7 dual vector and the VP2 vector in an attempt to determine if VP2 became associated with the core-like particles. No VP2 was detected on particles purified from insect cells expressing VP2, VP3 and VP7 (results not shown). Similar results were obtained in a parallel study using the VP3 and VP7 vector together with a recombinant baculovirus expressing VP5. Since neither of the capsid proteins attached individually to the core-like particles, a dual recombinant baculovirus was constructed which would express both VP2 and VP5 simultaneously.

Figure 4:
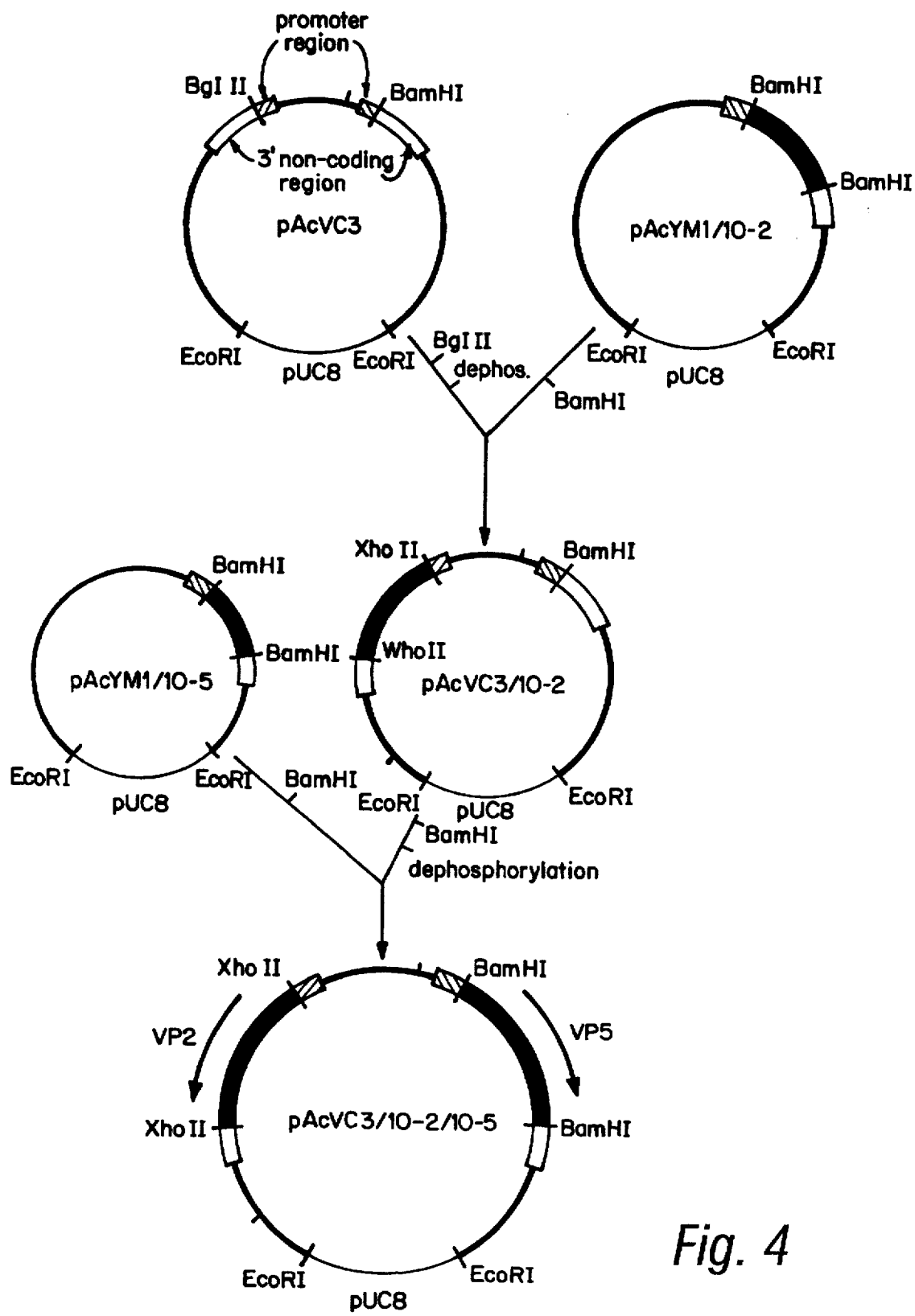
FIG. 4 shows the construction of baculovirus expression transfer vector containing the L2 and M5 genes of BTV serotype 10.

The manipulations for the construction of VP2-VP5 recombinant plasmid are shown in FIG. 4. They involved excision of the L2 and M5 genes from their pAcYMI single expression transfer vectors and insertion into the BamHI and BglII sites (respectively) of the multiple expression vector pAcVC3. Recombinant baculoviruses were prepared by the established procedure of co-transfecting S. frugiperda insect cells with the recombinant plasmid DNA and infectious wild-type AcNPV DNA. Progeny viruses were titrated using confluent monolayers of S. frugiperda cells and putative recombinants were selected on the basis of their polyhedrin-negative phenotype (ca 0.1% frequency). After successive rounds of plaque purification, a high titre viral stock was prepared.

Figure 5A:
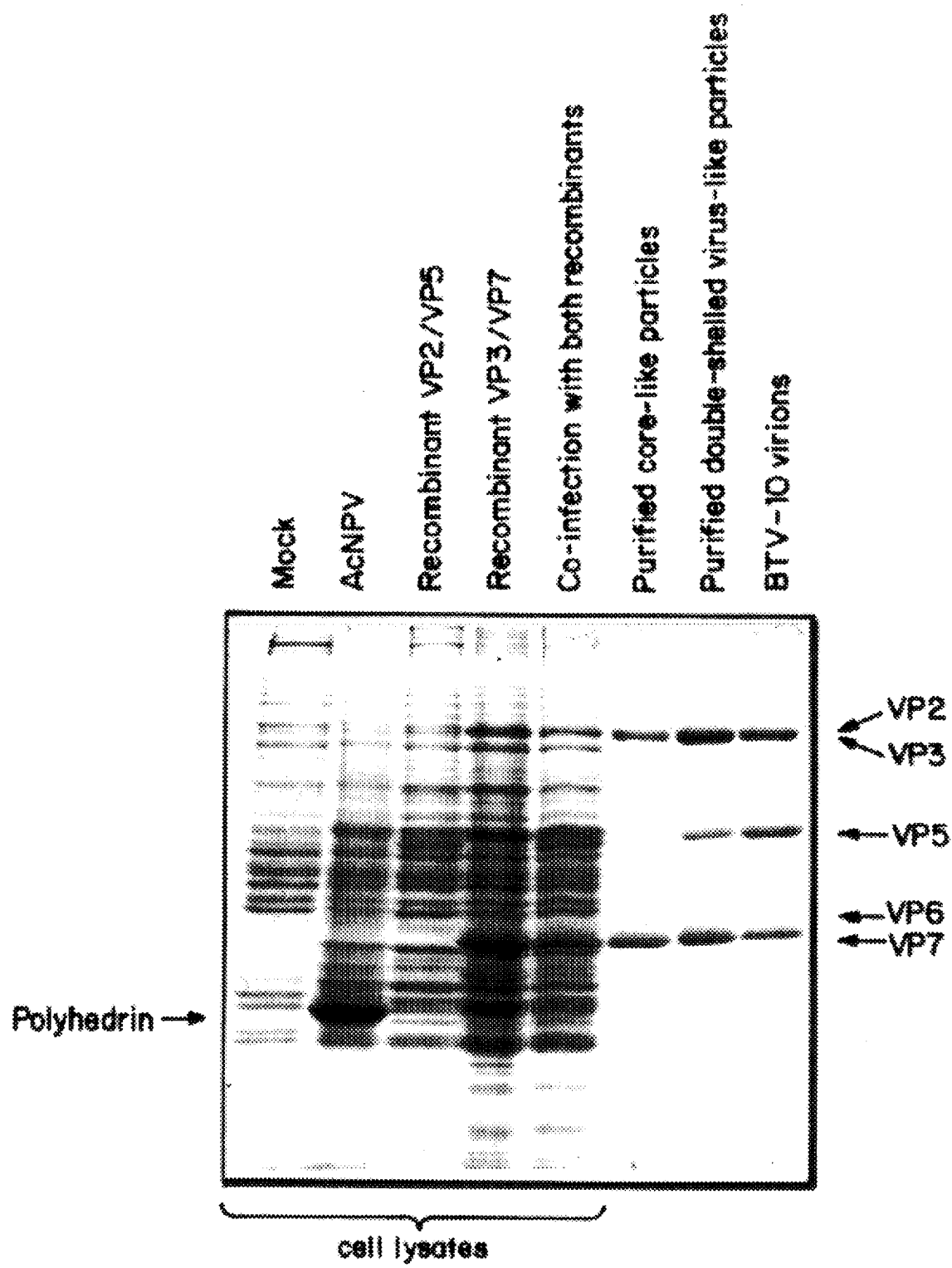
FIGS. 5A, 5B and 5C show the separation of proteins BTV VP2, BTV VP3, BTV VP7 by SDS-PAGE stained with Coomassie Blue (FIG. 5A), or electroblotted onto immobilon membrane and reacted with rabbit BTV 10 anti-serum (FIG. 5B), or reacted with anti-sera raised to expressed VP2 (FIG. 5C)
Figure 5B:
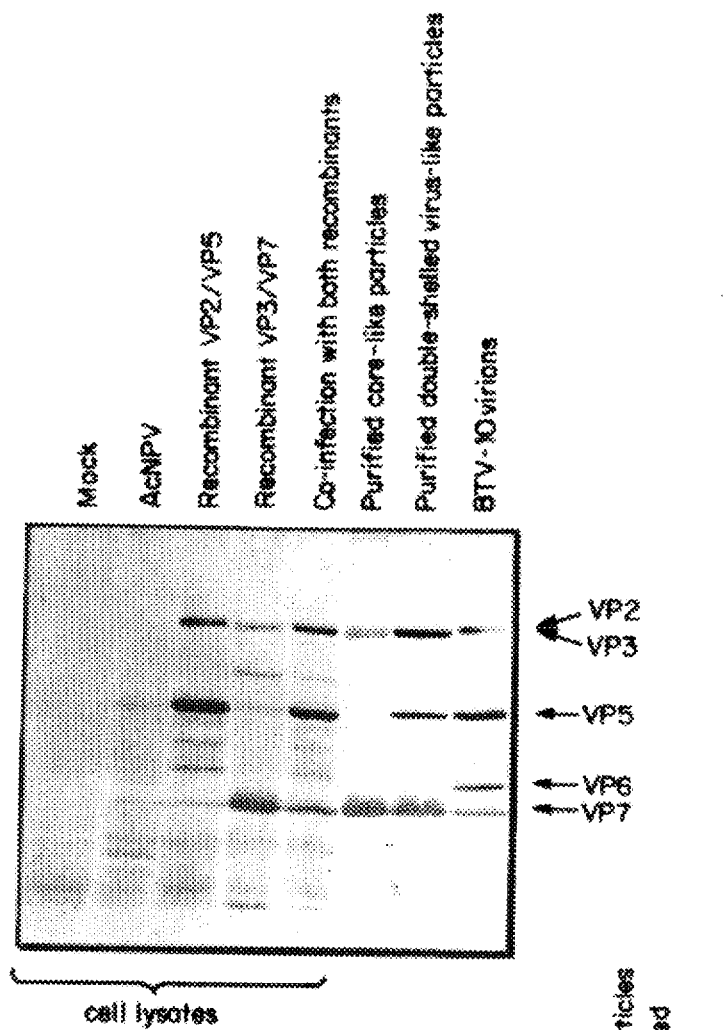

S. frugiperda cells infected with the recombinant baculovirus synthesized two unique protein species in place of the 29 KDa polyhedrin protein seen in wild-type AcNPV infected cells (FIG. 5A). The sizes of the expressed proteins agree with those expected of VP2 and VP5 calculated from their amino acid compositions (i.e., 111,112 Da and 59,136 Da respectively). Since the levels of expression were below that which could be determined by staining, confirmation that the expressed proteins represented authentic BTV proteins was provided by Western blot analyses using antisera raised to BTV-10 virus particles (FIG. 5B).

Although the outer capsid of BTV is composed of VP2 and VP5, no capsid-like structures were detected in insect cells infected with the VP2-VP5 recombinant baculovirus. To assess the interaction of these proteins with the BTV core-like particles, insect cells were co-infected with both dual recombinant baculoviruses (in order to co-express VP2, VP3, VP5 and VP7).

The cells were harvested at 48 hours post-infection, lysed with the non-ionic detergent NONIDET P40, and particles purified to homogeneity by centrifugation on discontinuous sucrose gradients. When examined under the electron microscope, empty double-shelled particles were observed consisting of a core surround by a thick outer capsid (FIG. 6A, large arrow). The diameters of the largest particles were estimated to be of the order of 85 nm, i.e., comparable to those of BTV (FIG. 6B). Some simple core-like particles were also observed in the preparation (FIG. 6A, thin arrows). Their diameters were estimated to be of the order of 65 nm. A range of intermediate structures were also observed, apparently with varying amounts of the outer capsid proteins attached. These may reflect different stages in particle assembly. Interestingly, the centre areas of both types of particles (cores, and virus-like particles) exhibited an icosahedral configuration. The smaller size of the central area of the virus-like particles is presumably due to the presence and density of the outer capsid proteins. The icosahedral configuration of the centre was also apparent in several authentic BTV particles where stain had penetrated the particles. The purified expressed particles were analysed by SDS-PAGE and Western Immunoblot and shown to contain large amounts of VP2 and VP5 (FIG. 5), in addition to VP3 and VP7.

The authenticity of the expressed empty double-shelled virus particles was assessed by their immunogenicity and haemagglutinating acitvity. Guinea pig sera raised against purified core-like particles and double-shelled virus-like particles were tested for their neutralizing activity against BTV-10. As expected, sera raised to the cores exhibited no neutralizing activity while in a 50% plaque reduction test substantial neutralization was demonstrated by the sera raised to the double-shelled particles at a dilution of 1:10, 000. Monospecific sera raised to VP2 gave titres of <500. Purified double-shelled particles also exhibited haemagglutinating titers (Table 1), comparable to those observed with authentic virus. Purified cores did not haemagglutinate. VP2 has been demonstrated to be the haemagglutinating protein in authentic bluetongue virus. These data are supported by the inhibitory effect of monospecific sera raised to VP2 on the haemagglutination activity of the double-shelled particles. Monspecific sera raised to the other component proteins (VP3, VP5 and VP7) had essentially no effect (Table 1). Unlike authentic BTV, the virus-like particles were non-infectious when assayed in mammalian cells.

Several interesting conclusions regarding BTV morphogenesis can be drawn from the results described herein. The outer capsid proteins VP2 and VP5 do not attach individually to the core-like particles. This suggests that these proteins .may interact before attaching to the core, or alternatively they may bind sequentially until a complete particle is produced. As with the formation of core-like particles in insect cells, the addition of the outer-capsid is not dependent on the presence of the BTV non-structural proteins (NS1, NS2, NS3), or viral double-stranded RNA, or the minor proteins VP1, VP4, VP6.

TABLE 1

Haemagglutination analysis of BTV double-shelled virus-like particles

| Substrate | Haemagglutination titer |
|---|---|
| Single-shelled core-like particles | <2 |
| Double-shelled virus-like particles | 2048 |

| Sera tested | Haemagglutination-Inhibition titer |
|---|---|
| Preimmune rabbit | 16 |
| Rabit anti VP2 | >1024 |
| Rabbit anti VP7 | 2 |
| Preimmune mouse | 4 |
| Mouse anti VP5 | 8 |
| Mouse anti VP3 | 32 |

S. frugiperda cells infected with the appropriate recombinant baculoviruses were lysed with Nonidet P-40 and double-shelled virus-like particles, or core-like particles, were isolated on discontinuous sucrose gradients. the haemagglutination titer of this material was assayed at 4° C. using 0.25% rabbit erythrocytes as the indicator. Titers are expressed as the reciprocal of the highest serial dilution that gave complete haemagglutination. Antisera raised to baculovirus expressed BTV proteins were used in haemagglutination-inhibition tests. The inhibition titers are expressed as the reciprocal of the highest serial dilution of sera that gave complete inhibition of haemagglutination.

FIGURE LEGENDS

FIG. 1. Construction diagram of the dual expression transfer vector showing the appropriate manipulations for the insertion of the BTV L3 and M7 genes.

FIG. 2. Expression of the BTV core proteins VP3 and VP7 in insect cells by the recombinant baculovirus, and confirmation of their authenticity by Western blot analysis. S. frugiperda cells were infected at a multiplicity of 10 pfu/cell with recombinant virus, wild-type AcNPV, or were mock infected. Cells were harvested at 48 h post-infection, washed with PBS and lysed at 4° C. in 50 mM Tris-Hcl pH 8.0, 150 mM NaCl, 0.5% NP40. The expressed particles were purified by banding at the interface of a 30% w/v, 50% w/v discontinuous sucrose gradient (in 0.2M Tris-HCI pH 8.0) after centrifugation at 85,000 rpm for 3 h. Authentic BTV virions and core particles prepared from BTV-infected BHK cells are included for comparison. Proteins were separated by SDS-PAGE and stained with Coomassie blue (A), or were electroblotted onto immobilon membrane, and reacted with rabbit anti BTV-10 serum (B). Bound antibody was detected with an alkaline phosphatase conjugate by the standard method.

FIG. 3. Electron micrographs of empty BTV core particles synthesized in insect cells by a recombinant baculovirus expressing both major BTV core proteins VP3 and VP7 (A) sections of S. frugiperda cells infected with the recombinant (1), or wild-type AcNPV virus (2). (B) purified expressed particles (3) compared with authentic BTV core particles (4).

FIG. 4C Construction of the baculovirus expression transfer vector containing the L2 and M5 genes of BTV serotype 10. The cloning, genetic manipulations, and individual expression of these genes have previously been described. The L2 and M5 genes were excised from their single baculovirus expression transfer vector (pAcYM1) and ligated into the BglII and BamHI sites respectively of the multiple expression vector pAcVC3.

Figure 5C:
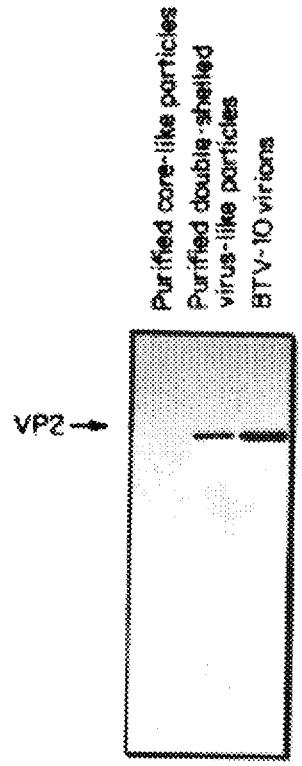
Figure 6A:
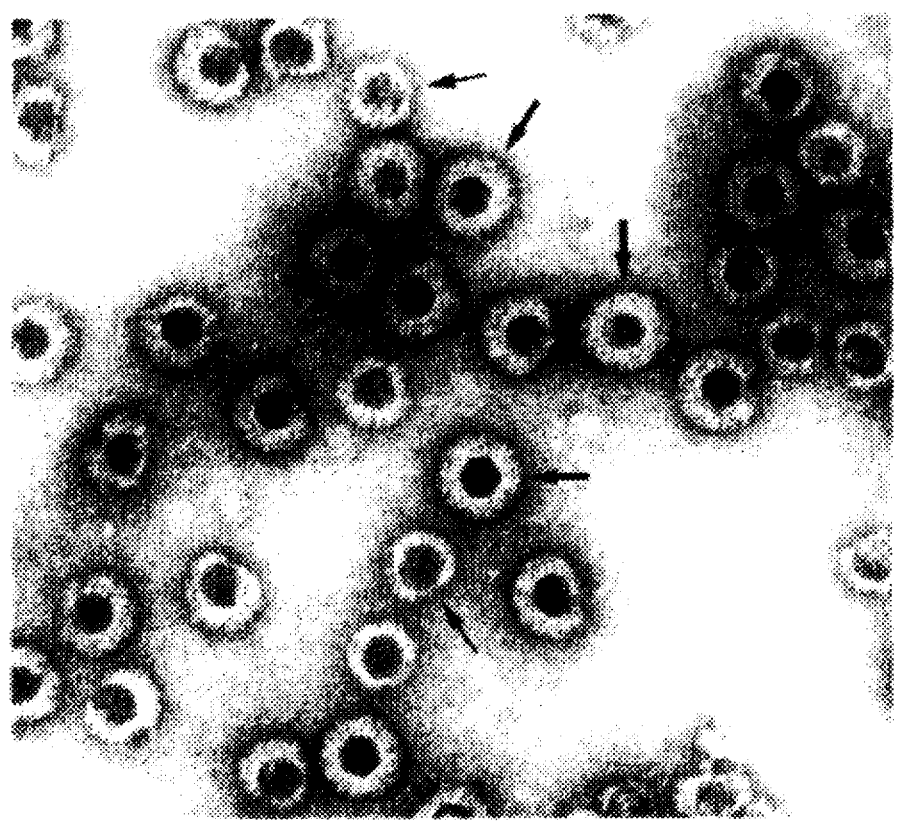
FIGS. 6A, 6B, 6C and 6D are electron micrographs of baculovirus expression particles, including empty BTV double-shelled virus-like particles (FIG. 6A), as compared to authentic BTV particles (FIG. 6B), expressed core-like particles composed of VP3 and VP7 (FIG. 6C), and double shelled particles with VP2 and VP5 attached to VP3 and VP7 (FIG. 6D).
Figure 6B:
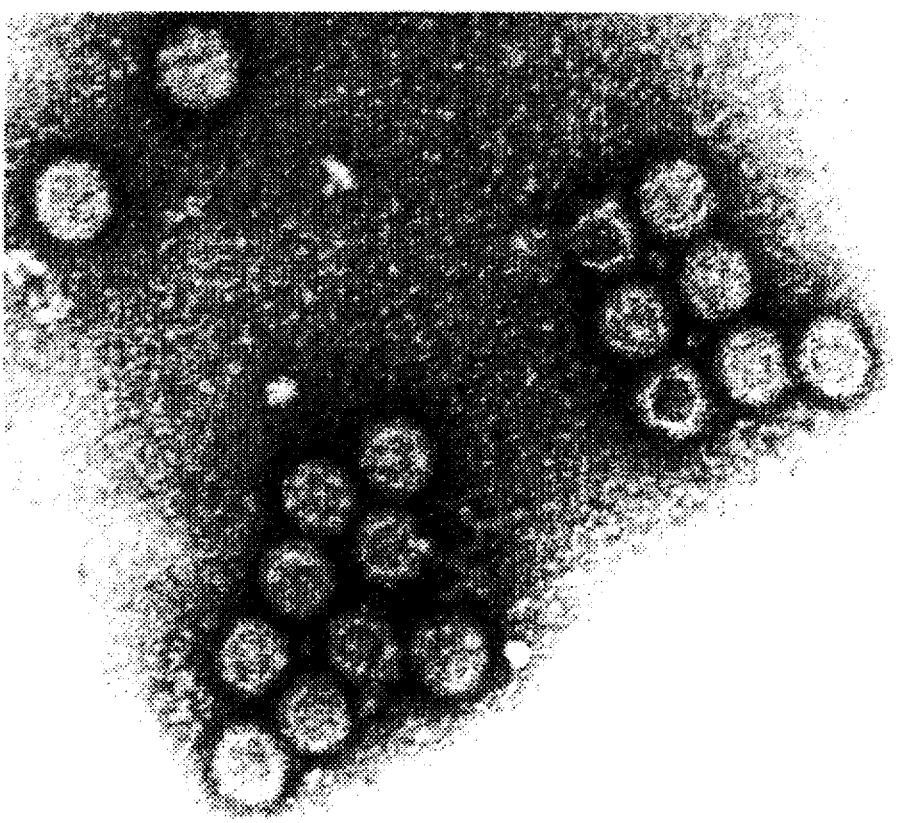
Figure 6C:
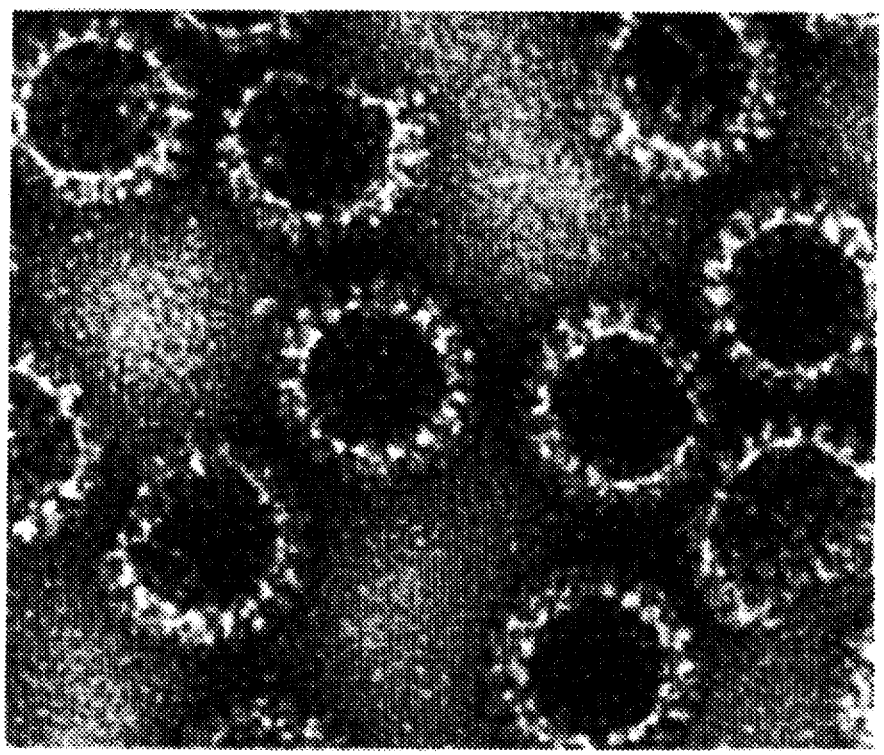
Figure 6D:
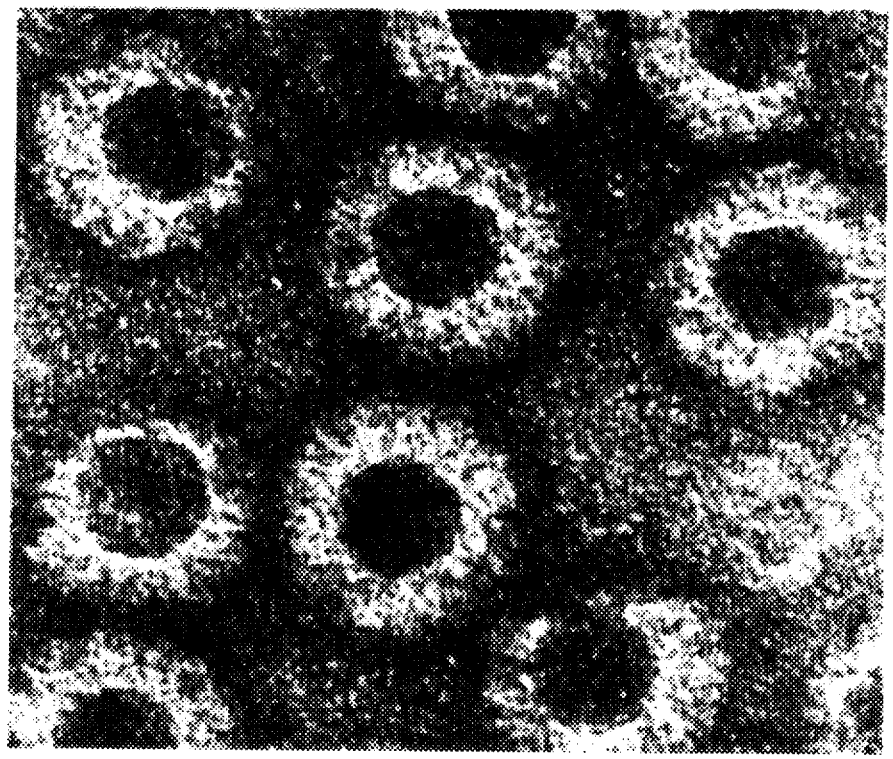

FIG. 5. Expression of the four major BTV structural proteins VP2, VP3, VP5 and VP7 in insect cells by recombinant baculoviruses, and confirmation of their authenticity by Western Immunoblot analysis. *S. frugiperda* cells were infected at a multiplicity of 5 pfu/cell with either the recombinant baculovirus expressing VP2 and VP5, or the recombinant expressing Vp3 and VP7, or were co-infected with both recombinant viruses. Mock and wild-type AcNPV infected cells acted as controls. Cells were harvested at 48 h post-infection, washed with PBS and lysed at 4° C. in 50 mM Tris-HCl pH8.0, 150 mM NaCl, 0–5% NP40. The expressed particles (both single-shelled core-like particles and double-shelled virus-like particles) were purified by banding at the interface of a 30% w/v, and 66% w/v discontinuous sucrose gradient (in 0.2M Tris-HCl, pH8.0) after centrifugation at 85,000 g for 3 h. Authentic BTV virions prepared from BTV-infected BHK cells are included for comparison. Proteins were separated by SDS-PAGE and stained with Coomassie Blue (A), or were electroblotted onto Immobilon membrane and reacted with rabbit BTV-10 antiserum (B). Since VP2 co-migrates with VP3, its presence in the purified double-shelled virus-like particles and authentic BTV virions was confirmed by reacting with antisera raised to expressed VP2 (C). Bound antibody was detected with an alkaline phosphatase conjugate using standard methods.

FIG. 6. Electron micrographs of baculovirus expressed particles. Empty BTV double-shelled virus-like particles are shown in (A) compared with authentic BTV particles (B). The high magnification micrographs (×30,000) show the appearance of expressed core-like particles composed of VP3 and VP7 (C), and the double-shelled particles with VP2 and VP5 attached to VP3 and VP7 (D).

We claim:

1. A process for preparing a Bluetongue Virus (BTV) capsid particle consisting of BTV VP3 and BTV VP7 comprising:
   (a) transforming a *S. frugiperda* cell with one or more vectors that mediate expression of BTV VP3 and the BTV VP7 proteins;
   (b) expressing said BTV VP3 and BTV VP7 proteins; and
   (c) isolating said capsid particle consisting of BTV VP3 and BTV VP7.

2. A process for preparing a Bluetongue Virus (BTV) capsid particle consisting of BTV VP3, BTV VP7, BTV VP2 and BTV VP5 comprising:
   (a) transforming a *S. frugiperda* cell with one or more vectors that mediate expression of BTV VP3, BTV VP7, BTV VP2 and BTV VP5 proteins;
   (b) expressing said BTV VP3, BTV VP7, BTV VP2 and BTV VP5 proteins; and
   (c) isolating said capsid particle consisting of BTV VP3, BTV VP7, BTV VP2 and BTV VP5.

3. A process according to claim 1, wherein said vector is a baculovirus expression vector.

4. A process according to claim 2, wherein said vector is a baculovirus expression vector.

* * * * *